(12) United States Patent
Shin et al.

(10) Patent No.: US 7,265,250 B2
(45) Date of Patent: Sep. 4, 2007

(54) METHOD OF PRODUCING UNSATURATED ALDEHYDE AND/OR UNSATURATED FATTY ACID

(75) Inventors: Hyun Jong Shin, Gwangju (KR); Yeon Shick Yoo, Seoul (KR); Byung Yul Choi, Naju-si (KR); Young Hyun Choi, Naju-si (KR); Young Jin Cho, Naju-si (KR); Duk Ki Kim, Gwangju (KR); Joo Yeon Park, Naju-si (KR); Kwang Ho Park, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 11/021,442

(22) Filed: Dec. 23, 2004

(65) Prior Publication Data

US 2005/0209484 A1    Sep. 22, 2005

(30) Foreign Application Priority Data

Dec. 26, 2003    (KR) ............ 10-2003-0097863

(51) Int. Cl.
*C07C 45/28* (2006.01)
*C07C 51/16* (2006.01)

(52) U.S. Cl. .................... 568/479; 562/547
(58) Field of Classification Search ............ None
See application file for complete search history.

(56) References Cited

U.S. PATENT DOCUMENTS 4,256,783 A    3/1981    Takada et al. ......... 422/197
5,198,581 A    3/1993    Kawajiri et al. ....... 562/546

FOREIGN PATENT DOCUMENTS

| JP | 53-030688 | 3/1978 |
| JP | 07-010802 | 1/1995 |
| JP | 11-080052 | 3/1999 |
| JP | 2001-129384 | 5/2001 |
| JP | 2001-137689 | 5/2001 |
| JP | 2001-139499 | 5/2001 |
| KR | 1020010080871 A | 8/2001 |

OTHER PUBLICATIONS

PCT International Search Report for Application No. PCT/KR2004/003433; International filing date: Dec. 24, 2004; Date of Mailing: Mar. 21, 2005.

*Primary Examiner*—Sikarl A. Witherspoon
(74) *Attorney, Agent, or Firm*—Cantor Colburn LLP

(57) ABSTRACT

Disclosed is a method for producing unsaturated aldehydes or unsaturated fatty acids from at least one compound selected from the group consisting of propylene, propane, (meth)acrolein, isobutylene, t-butyl alcohol, methyl-t-butyl ether and o-xylene by means of fixed-bed catalytic partial oxidation in a shell-and-tube reactor, characterized in that the reactor includes a reaction zone for producing unsaturated aldehydes as a main product, the reaction zone having an inactive material layer inserted into a position where a hot spot is to be generated in a reaction tube. A fixed-bed shell-and-tube reactor for use in the above method is also disclosed. According to the present invention, at least one layer of inactive material is packed at the point of a hot spot to control the hot spot temperature efficiently, thereby increasing the lifetime of a catalyst and producing unsaturated aldehydes and unsaturated fatty acids with high yield.

8 Claims, 2 Drawing Sheets

METHOD OF PRODUCING UNSATURATED ALDEHYDE AND/OR UNSATURATED FATTY ACID

TECHNICAL FIELD

The present invention relates to a method for producing unsaturated aldehydes and/or unsaturated acids from at least one compound selected from the group consisting of propylene, propane, (meth)acrolein, isobutylene, t-butyl alcohol, methyl-t-butyl ether and o-xylene, by means of fixed-bed catalytic partial oxidation in a shell-and-tube heat exchange type reactor, as well as to a fixed-bed shell-and-tube heat exchange type reactor used in the above method.

BACKGROUND ART

A process for producing unsaturated aldehydes and/or unsaturated acids from olefins is a typical example of catalytic vapor phase oxidation.

To perform the partial oxidation of olefins, a multimetal oxide containing molybdenum and bismuth or vanadium or a mixture thereof is used as a catalyst. Typically, the partial oxidation of olefins may be exemplified by a process for producing (meth)acrolein or (meth)acrylic acid by oxidizing propylene or isobutylene, a process for producing phthalic anhydride by oxidizing naphthalene or ortho-xylene or a process for producing maleic anhydride by partially oxidizing benzene, butylene or butadiene.

Generally, propylene or isobutylene is subjected to two-step catalytic vapor phase partial oxidation to form (meth) acrylic acid as a final product. More particularly, in the first step, propylene or isobutylene is oxidized by oxygen, diluted inert gas, water vapor and an optional amount of catalyst to form (meth)acrolein as a main product. In the second step, (meth)acrolein obtained from the preceding step is oxidized by oxygen, diluted inert gas, water vapor and an optional amount of catalyst to form (meth)acrylic acid. The catalyst used in the first step is an oxidation catalyst based on Mo—Bi, which oxidizes propylene or isobutylene to form (meth)acrolein as a main product. Additionally, a part of (meth)acrolein is further oxidized on the same catalyst to form acrylic acid partially. The catalyst used in the second step is an oxidation catalyst based on Mo—V, which oxidizes (meth)acrolein-containing mixed gas produced in the first step, particularly (meth)acrolein, to form (meth)acrylic acid as a main product.

Reactors for carrying out the above process are realized in such a manner that each of the above two steps are implemented in one system or in two different systems (see U.S. Pat. No. 4,256,783).

In general, catalytic vapor phase oxidation is implemented as follows. At least one catalyst in the form of granules is packed into reaction tubes, feed gas is supplied to a reactor through the reaction tubes and the feed gas is in contact with the catalyst in the reaction tubes to perform vapor phase oxidation. Reaction heat generated during the reaction is removed by heat transfer with a heat transfer medium, wherein the temperature of the heat transfer medium is maintained at a predetermined temperature. Particularly, the heat transfer medium for heat exchange is provided on the outer surface of the catalytic tubes to perform heat transfer. A reaction product mixture containing a desired product is collected via a duct and then sent to a purification step. Generally, catalytic vapor phase oxidation is a highly exothermic reaction. Therefore, it is very important to control the reaction temperature in a specific range and to downsize hot spots in the reaction zone.

For example, vapor phase partial oxidation of propylene or isobutylene using a metal oxide catalyst based on molybdenum-bismuth-iron is an exothermic reaction. Therefore, it has a problem in that a hot spot (a point whose temperature is abnormally high) is generated in the reactor. Such hot spots show a relatively high temperature compared to other parts of the reactor. Accordingly, in hot spots, complete oxidation proceeds rather than partial oxidation, thereby increasing by-products such as COx and decreasing the yield of (meth)acrylic acid and (meth)acrolein. Additionally, excessive heat generated in a hot spot causes migration of molybdenum that is a main element of the catalyst, resulting in deposition of molybdenum in a catalytic layer having a relatively low temperature and pressure drop in the catalytic layer, degradation of catalytic activity and in shortening of the lifetime of the catalyst. Therefore, yield of (meth) acrolein and (meth)acrylic acid decreases.

Generally, various methods are known in order to control the excessive heat at a hot spot in a catalytic reaction accompanied with heat generation. Such methods include a method for reducing the amount of feed gas to decrease the space velocity and a method of using a reaction tube having a relatively small inner diameter. However, when the space velocity decreases, it is not possible to obtain high productivity in an industrial scale. When the inner diameter of a reaction tube decreases, it is difficult to manufacture the reactor. Moreover, in the latter case, there are disadvantages of economically unfavorable high cost needed for manufacturing the reactor, and increased time and labor needed for packing a catalyst. For these reasons, there has been a continuous need for and research into a method for producing unsaturated aldehydes and/or unsaturated fatty acids with high yield and high productivity by using a catalyst stably for a long time, while avoiding the above problems according to the known methods.

According to the prior art, disclosed is a reactor for producing unsaturated aldehydes and/or unsaturated fatty acids with high yield over a long time while extending the lifetime of a catalyst, by controlling the excessive reaction heat at the hot spot and optimizing catalytic activity and selectivity. Japanese Laid-Open Patent Nos. Sho53-30688B1 and Hei7-10802A1 disclose a fixed-bed reactor including a reaction zone for the first step of producing acrolein as a main product, the reaction zone comprising a catalytic bed that is formed of a catalyst mixed and diluted with an inactive material and is packed in such a manner that the ratio of the inactive material gradually decreases from the inlet of the reactor toward the outlet of the reactor, i.e., in the direction of reaction gas flow.

U.S. Pat. No. 5,198,581 discloses a fixed-bed multi-tube type reactor for producing unsaturated aldehydes and unsaturated fatty acids by means of catalytic vapor phase oxidation of at least one compound selected from the group consisting of propylene, isobutylene, t-butyl alcohol and methyl-t-butyl ether with molecular oxygen or molecular oxygen-containing gas. The above reactor includes a plurality of reaction zones each packed with a different composite oxide-based catalyst having a different occupation volume along the axial direction of each reaction tube, wherein the volume is controlled so that it decreases from the gas inlet to the outlet. Korean Laid-Open Patent No. 2001-80871 discloses a method for producing acrolein (ACR) and acrylic acid (AA) by means of vapor phase oxidation of propylene with molecular oxygen or molecular oxygen-containing gas in a fixed-bed cylindrical reactor.

According to the above method, a plurality of catalysts having different activities are obtained by controlling (a) the volume occupied by a catalyst, (b) sintering temperature, and/or (c) kind and/or amount of alkali metal elements. Additionally, the catalytic bed in each reaction tube is divided into two or more reaction zones along the axial direction, the reaction zones being packed with the catalysts in such a manner that the catalytic activity increases from the reaction gas inlet to the outlet.

As described in the prior art, the method for packing a catalyst after it is mixed and diluted with an inactive material, the method for packing a plurality of composite oxide-based catalysts having different occupation volumes in such a manner that the volume gradually decreases, etc., have problems in that they are inefficient for commercial use because the packing ratio of a catalyst varies depending on the size, shape, specific gravity and density of the catalyst and inactive material, even though the catalyst is mixed and diluted with the inactive material at a correct ratio and then the mixture is packed into a reaction tube. Additionally, the method for packing a catalyst by controlling the catalytic activity through the control of the occupation volume, sintering temperature and/or kind and/or amount of alkali metal elements in the catalyst having a specific composition can reduce the temperature of a hot spot generated during the catalytic reaction, thereby minimizing degradation of catalyst and side reactions. However, the method is problematic in that the hot spot still maintains high temperature.

Therefore, there is a continuous need for a method for minimizing degradation of catalyst and side reactions caused by extreme heat generation at a hot spot generated during the catalytic reaction.

DISCLOSURE OF THE INVENTION

Figure 1:
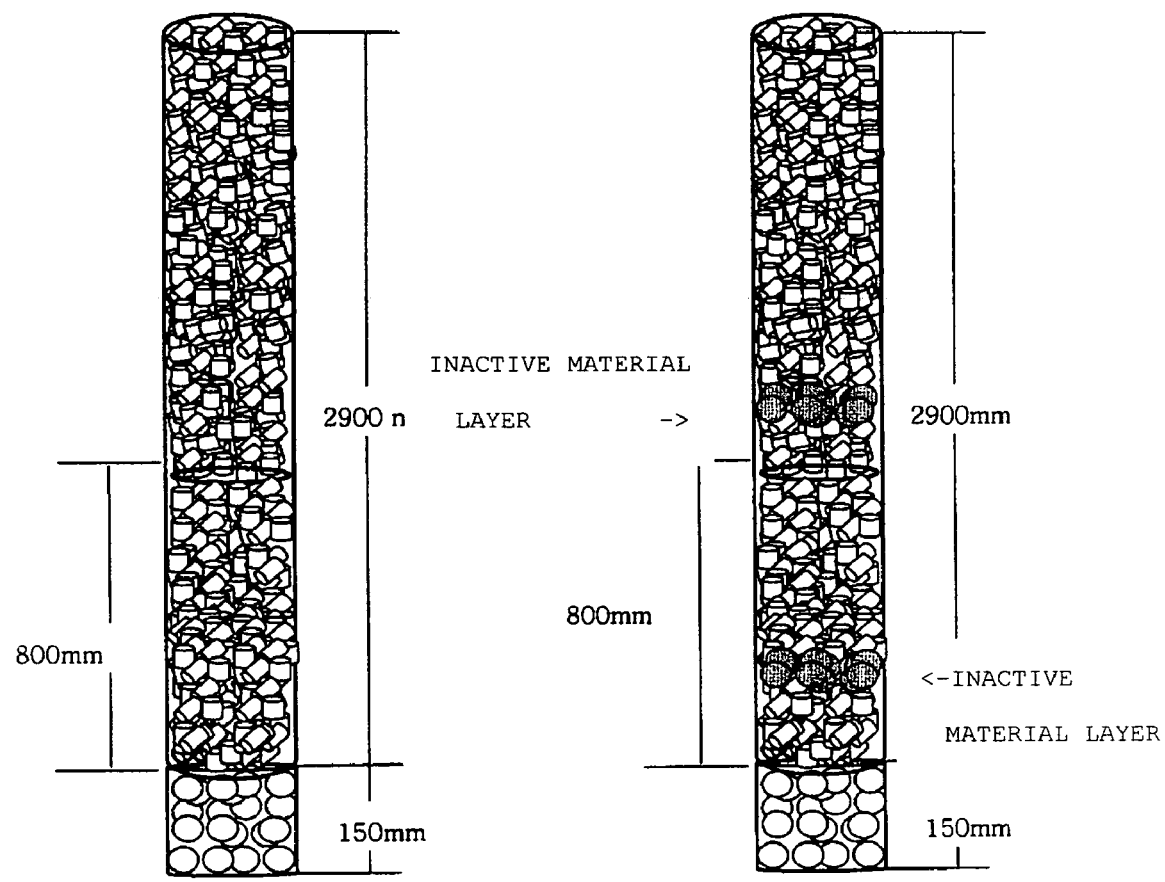
FIG. 1 is a schematic view showing the structure of a reactor according to Example 2, including catalytic layers and an inactive material layer packed therein.

It is an object of the present invention to provide a method for producing unsaturated aldehydes and/or unsaturated fatty acids with high yield in a stable manner for a long time, the method including estimating the position of a hot spot in a reaction tube and packing an inactive material layer into the hot spot to reduce heat generation at the hot spot, thereby facilitating heat control and/or to disperse a temperature distribution toward a reaction gas outlet.

According to an aspect of the present invention, there is provided a method for producing unsaturated aldehydes or unsaturated fatty acids from at least one compound selected from the group consisting of propylene, propane, (meth) acrolein, isobutylene, t-butyl alcohol, methyl-t-butyl ether and o-xylene by means of fixed-bed catalytic partial oxidation in a shell-and-tube reactor, characterized in that the reactor includes a reaction zone for producing unsaturated aldehydes as a main product, the reaction zone having an inactive material layer inserted into a position where a hot spot is to be generated in a reaction tube.

According to another aspect of the present invention, there is provided a shell-and-tube reactor that may be used in a method for producing unsaturated aldehydes or unsaturated fatty acids from at least one compound selected from the group consisting of propylene, propane, (meth)acrolein, isobutylene, t-butyl alcohol, methyl-t-butyl ether and o-xylene by means of fixed-bed catalytic partial oxidation, characterized in that the reactor includes a reaction zone for producing unsaturated aldehydes as a main product, the reaction zone having an inactive material layer inserted into a position where a hot spot is to be generated in a reaction tube.

Hereinafter, the present invention will be explained in detail.

According to the present invention, an inactive material layer is formed at the position of a hot spot in the reactor so that partial oxidation at the hot spot can be prevented, thereby minimizing heat generation at the hot spot and dispersing the temperature distribution, resulting in minimization of degradation of catalyst and side reactions.

As used herein, the term "hot spot" is referred to as a point where a peak temperature is generated. For example, a hot spot may be a point where an abnormally high temperature is maintained due to excessive heat generation or heat accumulation, in a catalytic bed in the reaction tube of the first-step reaction zone for producing unsaturated aldehydes as a main product.

A hot spot is formed by the reaction heat generated during catalytic vapor phase oxidation. The position and size of a hot spot are determined by many factors including a reactant composition, space velocity and temperature of heat transfer medium. Under constant processing conditions, a hot spot has a constant position and size. Therefore, the position of a hot spot can be estimated by using a simulation method, etc.

In general, each catalytic layer has at least one hot spot. The hot spot in the first-step reaction zone may be generated at the front part of the catalytic bed for the first-step oxidation, enriched with a main reactant and molecular oxygen. In addition, the hot spot may be generated at the vicinity of the border of adjacent catalytic layers having different activities, in the case of a reactor structure packed with two or more catalytic layers in the first-step reaction zone.

Figure 2:
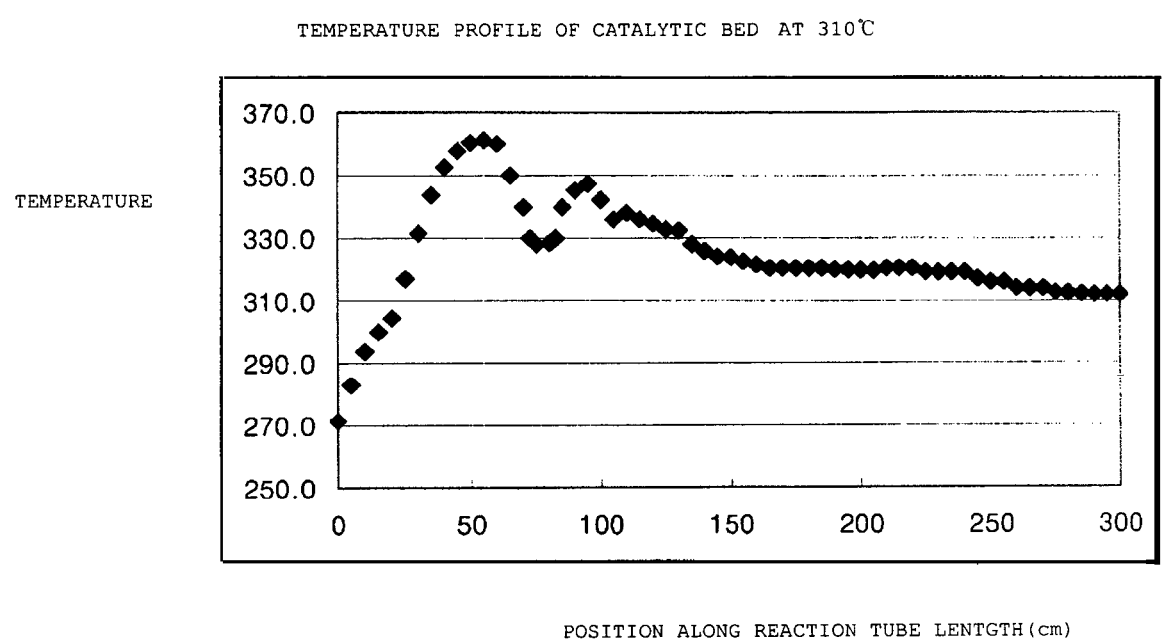
FIG. 2 is a graph showing the temperature profile of a catalyst bed at 310° C. in the first-step reaction producing unsaturated aldehyde as a main product.

According to the present invention, the position of a hot spot and the temperature peak size of a hot spot are quantitatively analyzed based on the temperature profile (see FIG. 2) of a catalytic bed in a reaction tube. Then, a predetermined height of an inactive material layer is inserted into the temperature peak position where a hot spot is generated so as to prevent partial oxidation at the hot spot, thereby minimizing heat generation at the hot spot and dispersing a temperature distribution.

The reactors that may be used in the present invention include a fixed-bed multi-tube reactor and a conical fixed-bed multi-tube reactor. There is no particular limitation on the shape of the reactor. In order to form a catalytic bed needed for carrying out vapor phase partial oxidation, a catalyst is packed in the reaction tube of a reactor, an inactive material is packed at the position of a hot spot, in one layer or two or more layers having different kinds and sizes of inactive material, and then the catalyst is further packed in the reaction tube.

In the case of the first-step reaction zone for producing unsaturated aldehydes as a main product, a catalytic bed may be packed in one layer having uniform activity along the axial direction, or in two or more layers whose catalytic activity gradually increases along the axial direction, if necessary.

Preferably, the catalyst used in the vapor phase partial oxidation for producing unsaturated aldehydes as a main product is a metal oxide represented by the following formula 1:

$$Mo_aA_bB_cC_dD_eE_fF_gO_h \qquad \text{[formula 1]}$$

wherein Mo is molybdenum;

A is at least one element selected from the group consisting of Bi and Cr;

B is at least one element selected from the group consisting of Fe, Zn, Mn, Cu and Te;

C is at least one element selected from the group consisting of Co, Rh and Ni;

D is at least one element selected from the group consisting of W, Si, Al, Zr, Ti, Cr, Ag and Sn;

E is at least one element selected from the group consisting of P, Te, As, B, Sb, Nb, Mn, Zn, Ce and Pb;

F is at least one element selected from the group consisting of Na, K, Li, Rb, Cs, Ta, Ca, Mg, Sr, Ba and MgO; and each of a, b, c, d, e, f and g represents the atomic ratio of each element, with the proviso that when a=10, b is a number of between 0.01 and 10, c is a number of between 0.01 and 10, d is a number of between 0.0 and 10, e is a number of between 0.0 and 10, f is a number of between 0 and 20, g is a number of between 0 and 10, and h is a number defined depending on the oxidation state of each of the above elements.

The catalyst may have a cylindrical or a hollow cylindrical shape, and there is no particular limitation in shape of the catalyst. The catalyst preferably has an aspect ratio (the ratio of length to diameter (outer diameter), i.e., L/D) of between 1 and 1.3. More preferably, the ratio of L/D equals 1.

The inactive material layer that may be used in the present invention may be formed of an inactive material alone or a mixture of an inactive material with a catalyst. However, when a mixture of an inactive material with a catalyst is used, the activity of the mixture should be lower than that of a catalytic layer in the vicinity of a hot spot. The volume ratio of the inactive material to the catalyst in the inactive material layer is preferably 20-100%, and more preferably 80-100%.

The inactive material that may be used in the present invention is referred to as material inactive to a reaction for producing unsaturated aldehydes and/or unsaturated acids such as catalytic oxidation of propylene/isobutylene. Such inactive materials include silica, alumina, silica/alumina, zirconium oxide, titanium oxide, mixtures thereof, etc.

Although there is no particular limitation in shape of the inactive material, the inactive material may have the shape of a sphere, cylinder, ring, rod, plate, iron net and mass with a suitable size. If necessary, mixtures of the above shapes may be used.

When the inactive material has the shape of a sphere, cylinder and ring, the diameter is preferably 2-10 mm, and more preferably 5-8 mm. When the inactive material has the shape of a cylinder and ring, the ratio of length to diameter (L/D) is preferably 1-1.3, and more preferably is 1. Preferably, the inactive material has the same or similar shape and/or size as the catalyst.

At the point of a hot spot, the inactive material layer is packed to the height of 0.1-1000 mm, preferably to the height of 10-200 mm, in one or more layers, preferably in one or two layers. The position where the inactive material layer is disposed in a reaction tube ranges preferably 1-70% and more preferably 1-50% of the total length of the whole catalytic bed in the reaction zone producing unsaturated aldehyde as a main product, when viewed from the reaction gas inlet toward the outlet.

It is preferable that the temperature at the hot spot of a reactor is controlled by the inactive material layer inserted into the hot spot, in such a manner that the temperature of the hot spot is equal to or lower than (reaction temperature +55° C.). Accordingly, it is possible to minimize volatilization of catalytically active components and to inhibit side reactions caused by excessive heat, thereby increasing the lifetime of a catalyst and producing unsaturated aldehydes and unsaturated fatty acids with high yield.

Vapor phase partial oxidation for producing aldehydes as a main product in a reactor having an inactive layer at the hot spot according to the present invention is suitably carried out at a reaction temperature of 200-450° C., preferably 200-370° C., under a reaction pressure of 0.1-10 atm, preferably 0.5-3 atm. For example, in order to perform oxidation, a feed gas including 5-10 volume % of a feed compound such as propylene, 13 volume % of oxygen, 5-60 volume % of water vapor and 20-80 volume % of an inert gas is introduced onto a catalyst at a space velocity of 500-5000 hr$^{-1}$ (STP).

MODE FOR CARRYING OUT THE INVENTION

Reference will now be made in detail to the preferred embodiments of the present invention. It is to be understood that the following examples are illustrative only and the present invention is not limited thereto.

Preparation Example 1

(Preparation of Catalyst)

2500 ml of distilled water was heated with stirring at 70-85° C. and 1000 g of ammonium molybdate was dissolved therein to form solution (1). To 400 ml of distilled water, 274 g of bismuth nitrate, 228 g of iron nitrate and 1.9 g of potassium nitrate were added and mixed thoroughly. Next, 71 g of nitric acid was added to the mixture and dissolved therein to form solution (2). 618 g of cobalt nitrate was dissolved in 200 ml of distilled water to form solution (3). Solution (2) was mixed with solution (3) and the combined solution was further mixed with solution (1), while maintaining the temperature of the solution at 40-60° C., to form a catalyst suspension.

The suspension obtained as described above was dried to provide $Mo_{12}Bi_{1.2}Fe_{1.2}Co_{4.5}K_{0.04}$, which was pulverized into a size of 150 μm or less. The pulverized catalyst powder was mixed for 2 hours and formed into a cylindrical shape. The formed catalyst had an outer diameter of 4.0-8.0 mm. Then, the catalyst was baked at 500° C. for 5 hours under air to check the catalytic activity.

Comparative Example 1

To a stainless steel reactor having an inner diameter of 1 inch and heated with molten nitrate, alumina/silica as an inactive material was packed to the height of 150 mm, and then the catalyst obtained from Preparation Example 1 and having a size of 5 mm(±0.2) was packed to the height of 2900 mm, when viewed from the reaction gas inlet toward the outlet.

Example 1

To a stainless steel reactor having an inner diameter of 1 inch and heated with molten nitrate, alumina/silica as an inactive material was packed to the height of 150 mm, the catalyst obtained from Preparation Example 1 and having a size of 5 mm(±0.2) was packed to the height of 200 mm, alumina/silica as an inactive material was packed to the height of 100 mm at the point of a hot spot, and then the catalyst obtained from Preparation Example 1 and having a size of 5 mm(±0.2) was further packed to the height of 2600 mm, when viewed from the reaction gas inlet toward the outlet.

Comparative Example 2

To a stainless steel reactor having an inner diameter of 1 inch and heated with molten nitrate, alumina/silica as an inactive material was packed to the height of 150 mm, the catalyst obtained from Preparation Example 1 and having a size of 7 mm(±0.2) was packed to the height of 800 mm, and then the catalyst obtained from Preparation Example 1 and having a size of 5 mm(±0.2) was further packed to the height of 2100 mm, when viewed from the reaction gas inlet toward the outlet.

Example 2

To a stainless steel reactor having an inner diameter of 1 inch and heated with molten nitrate, alumina/silica as an inactive material was packed to the height of 150 mm, the catalyst obtained from Preparation Example 1 and having a size of 7 mm(±0.2) was packed to the height of 200 mm, alumina/silica as an inactive material was packed to the height of 100 mm at the point of a hot spot, and then the catalyst obtained from Preparation Example 1 and having a size of 7 mm(±0.2) was further packed to the height of 500 mm, when viewed from the reaction gas inlet toward the outlet. Further, the catalyst obtained from Preparation Example 1 and having a size of 5 mm(±0.2) was packed to the height of 100 mm, alumina/silica as an inactive material was packed to the height of 100 mm at the point of a hot spot, and then the catalyst obtained from Preparation Example 1 and having a size of 5 mm(±0.2) was packed to the height of 1900 mm.

Comparative Example 3

To a stainless steel reactor having an inner diameter of 1 inch and heated with molten nitrate, alumina/silica as an inactive material was packed to the height of 150 mm, the catalyst obtained from Preparation Example 1 and having a size of 7 mm(±0.2) was packed to the height of 800 mm, the catalyst obtained from Preparation Example 1 and having a size of 4.5 mm(±0.2) was packed to the height of 1100 mm, and then the catalyst obtained from Preparation Example 1 and having a size of 5 mm(±0.2) was packed to the height of 1000 mm, when viewed from the reaction gas inlet toward the outlet.

Example 3

To a stainless steel reactor having an inner diameter of 1 inch and heated with molten nitrate, alumina/silica as an inactive material was packed to the height of 150 mm, the catalyst obtained from Preparation Example 1 and having a size of 7 mm(±0.2) was packed to the height of 200 mm, alumina/silica as an inactive material was packed to the height of 100 mm at the point of a hot spot, and then the catalyst obtained from Preparation Example 1 and having a size of 7 mm(±0.2) was further packed to the height of 500 mm, when viewed from the reaction gas inlet toward the outlet. Next, the catalyst obtained from Preparation Example 1 and having a size of 4.5 mm(±0.2) was packed to the height of 100 mm, alumina/silica as an inactive material was packed to the height of 100 mm at the point of a hot spot, and then the catalyst obtained from Preparation Example 1 and having a size of 4.5 mm(±0.2) was packed to the height of 900 mm. Further, the catalyst obtained from Preparation Example 1 and having a size of 5 mm(±0.2) was packed to the height of 100 mm, alumina/silica as an inactive material was packed to the height of 100 mm at the point of a hot spot, and then the catalyst obtained from Preparation Example 1 and having a size of 5 mm(±0.2) was packed to the height of 800 mm.

Comparative Example 4

The same catalyst, inactive material and packing heights as Comparative Example 3 were used to provide a reactor, except that a stainless steel fixed-bed conical multi-tube reactor was used instead of the stainless steel reactor having an inner diameter of 1 inch.

Example 4

The same catalyst, inactive material and packing heights as Example 3 were used to provide a reactor, except that a stainless steel fixed-bed conical multi-tube reactor was used instead of the stainless steel reactor having an inner diameter of 1 inch.

Experimental Example

Catalytic Activity Test

The reactors packed with catalysts according to the above Examples and Comparative Examples were used to perform oxidation of propylene, thereby producing acrolein and acrylic acid. The oxidation was carried out by introducing a feed gas containing 7 volume % of propylene, 13 volume % of oxygen, 8 volume % of water vapor and 73 volume % of inert gas onto the catalyst at the reaction temperature of 320° C., under the reaction pressure of 0.7 atm, at the space velocity of 1400 $hr^{-1}$ (STP).

The results obtained from the above Examples and Comparative Examples are shown in the following Table 1.

In Table 1, the reactant (propylene) conversion ratio, selectivity and yield are calculated based on the following mathematical formulae 1 and 2.

propylene conversion ratio(%)=[moles of reacted propylene/moles of supplied propylene] ×100   [Mathematical Formula 1]

yield(%) of acrolein+acrylic acid=[moles of produced acrolein and acrylic acid/moles of supplied propylene]×100   [Mathematical Formula 2]

TABLE 1

| Examples | Propylene Conversion (%) | Highest Hot Spot Temperature (° C.) | Yield of Acrolein + Acrylic Acid (%) |
|---|---|---|---|
| Comp. Ex. 1 | 96.21 | 385 | 88.45 |
| Ex. 1 | 96.75 | 368 | 90.38 |
| Comp. Ex. 2 | 96.67 | 380 | 89.39 |
| Ex. 2 | 96.97 | 368 | 90.41 |
| Comp. Ex. 3 | 97.34 | 375 | 89.76 |

TABLE 1-continued

| Examples | Propylene Conversion (%) | Highest Hot Spot Temperature (° C.) | Yield of Acrolein + Acrylic Acid (%) |
|---|---|---|---|
| Ex. 3 | 97.37 | 365 | 91.22 |
| Comp. Ex. 4 | 97.25 | 352 | 89.56 |
| Ex. 4 | 98.15 | 351 | 90.38 |

As can be seen from Table 1, reactors of Examples 1-4 including at least one layer of inactive material formed at the point of a hot spot in the catalytic reaction zone according to the present invention can provide excellent propylene conversion ratio and yield of a desired product as well as a lower temperature in the point of heat generation.

INDUSTRIAL APPLICABILITY

As can be seen from the foregoing, the present invention provides a method for producing unsaturated aldehydes and/or unsaturated fatty acids from at least one compound selected from the group consisting of propylene, propane, (meth)acrolein, isobutylene, t-butyl alcohol, methyl-t-butyl ether and o-xylene, by means of fixed-bed catalytic vapor phase partial oxidation with molecular oxygen or molecular oxygen-containing gas in a shell-and-tube heat exchange type reactor. According to the present invention, it is possible to minimize the heat generation in hot spots, to disperse a temperature distribution toward an outlet, and thus to produce unsaturated aldehydes and unsaturated fatty acids stably with high yield for a long time, by virtue of at least one layer of inactive material inserted at the point of a hot spot.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A method for producing unsaturated aldehydes or unsaturated fatty acids from at least one compound selected from the group consisting of propylene, propane, (meth) acrolein, isobutylene, t-butyl alcohol, methyl-t-butyl ether and o-xylene by means of fixed-bed catalytic partial oxidation in a shell-and-tube reactor, the reactor having at least one catalytic layer for producing unsaturated aldehydes as a main product in a reaction tube, characterized in that an inactive material layer is inserted into the catalytic layer(s) at a position where a hot spot is to be generated in a reaction tube.

2. The method according to claim 1, wherein the catalyst is a metal oxide catalyst represented by the following formula 1:

$$Mo_a A_b B_c C_d D_e E_f F_g O_h \quad \text{[formula 1]}$$

wherein Mo is molybdenum;
A is at least one element selected from the group consisting of Bi and Cr;
B is at least one element selected from the group consisting of Fe, Zn, Mn, Cu and Te;
C is at least one element selected from the group consisting of Co, Rh and Ni;
D is at least one element selected from the group consisting of W, Si, Al, Zr, Ti, Cr, Ag and Sn;
E is at least one element selected from the group consisting of P, Te, As, B, Sb, Nb, Mn, Zn, Ce and Pb;
F is at least one element selected from the group consisting of Na, K, Li, Rb, Cs, Ta, Ca, Mg, Sr, Ba and MgO; and
each of a, b, c, d, e, f and g represents the atomic ratio of each element, with the proviso that when a=10, b is a number of between 0.01 and 10, c is a number of between 0.01 and 10, d is a number of between 0.0 and 10, e is a number of between 0.0 and 10, f is a number of between 0 and 20, g is a number of between 0 and 10, and h is a number defined depending on the oxidation state of each of the above elements.

3. The method according to claim 1, wherein the inactive material layer is formed of an inactive material alone or a mixture of an inactive material with a catalyst.

4. The method according to claim 3, wherein the inactive material is present in the inactive material layer in a ratio of between 20% and 100% based on the volume of the catalyst.

5. The method according to claim 1, wherein the inactive material layer is packed to a height of between 0.1 mm and 1000 mm.

6. The method according to claim 3, wherein the inactive material takes a spherical, cylindrical or ring shape and has a diameter of between 2 mm and 10 mm.

7. The method according to claim 1, wherein the temperature of the hot spot is controlled in such a manner that it is equal to or lower than (reaction temperature +55° C.).

8. The method according to claim 1, wherein the inactive material has the same size, shape or size and shape as the catalyst.

* * * * *